United States Patent [19]

Bevilacqua et al.

[11] Patent Number: 5,827,837
[45] Date of Patent: Oct. 27, 1998

[54] POLYANION ANTI-INFLAMMATORY AGENTS

[75] Inventors: Michael P. Bevilacqua, Boulder; Richard M. Nelson, Lafayette, both of Colo.; Oliviero Cecconi, Del Mar, Calif.

[73] Assignee: The Regents of the University of California, Oakland, Calif.

[21] Appl. No.: 601,057

[22] PCT Filed: Aug. 19, 1994

[86] PCT No.: PCT/US94/09492

§ 371 Date: Sep. 3, 1996

§ 102(e) Date: Sep. 3, 1996

[87] PCT Pub. No.: WO95/05830

PCT Pub. Date: Mar. 2, 1995

Related U.S. Application Data

[63] Continuation-in-part of Ser. No. 109,642, Aug. 20, 1993, abandoned.

[51] Int. Cl.⁶ .................................................. A61K 31/66
[52] U.S. Cl. ........................... 514/103; 514/126; 514/517
[58] Field of Search ...................... 514/103, 126, 514/506, 517

[56] References Cited

U.S. PATENT DOCUMENTS

| | | | |
|---|---|---|---|
| 4,794,014 | 12/1988 | Siren | 426/547 |
| 5,019,566 | 5/1991 | Siren | 514/103 |
| 5,051,411 | 9/1991 | Siren | 514/103 |
| 5,128,332 | 7/1992 | Siren et al. | 514/103 |
| 5,143,716 | 9/1992 | Unger | 424/9 |
| 5,274,161 | 12/1993 | Siren et al. | 558/155 |
| 5,318,890 | 6/1994 | Rosen | 435/7.24 |

FOREIGN PATENT DOCUMENTS

| | | |
|---|---|---|
| 0 508 488 A2 | 10/1992 | European Pat. Off. . |
| 92/00079 | 1/1992 | WIPO . |

OTHER PUBLICATIONS

Mulligan MS et al. Nature. 364, 149–151, Jul. 1993.
Benesch, et al., *The Anostetic Effect of Mositor Hexasulfate on Oxygen Binding By Hemglobin*, Biochemistry, 15(15):3396, 1976.
Claxson, et al., *The anti-inflammatory effects of D-myo-inositol-1.2.6-trisphosphate (PP56) on animal models of inflammation*, Agents and Actions, 29(1/2):68, 1990.
Dabora et al., *Effect of Polyanions on the Refolding of Human Acidic Fibroblast Growth Factor\**, The Journal of Biological Chemistry, 266(35):23637, 1991.
Siren (I), et al., *Pharmacological Effects of D-myo-Inositol-1,2,6-Trisphosphate*, Inositol Phosphates and Derivatives, Chapter 7, pp. 103–120, 1991.
Eggleton, et al., *Priming action of inositol hexakisphosphate (InsP6) on the stimulated respiratory burst in human neutrophils*, Chimicia et Biophysica Acta, 1094:309, 1991.
Menniti et al., *Turnover of Inositol Polyphosphate Pyrophosphates in Pancreatoma Cells*, The Journal of Biological Chemistry, 265(6):3850, 1990.
Nelson, W.J., *Generation of plasma membrane in polarized epithelial cells: role of cell–cell contacts and assembly of the membrane cytoskeleton*, Cytoskeleton: its Role in Cellular Function, vol. 19, 1991.
Stephens, et al., *The Detection, Purification, Structural Characterization, and Metabolism of Diphosphoinositol Pentakisphosphate(s) and Bisdiphosphoinositol Tetrakisphosphate(s)\**, The Journal of Biological Chemistry, 268(6):4009, 1993.
Szwergold et al., *Observation of Inositol Pentakis–and Hexakis–Phosphate in Mammalian Tissues by 31PP NMR*, Biochemical and Biophysical Research Communications, 149(3):874, 1987.

*Primary Examiner*—Evelyn Huang
*Attorney, Agent, or Firm*—Fish & Richardson P.C.

[57] ABSTRACT

Selectin binding and inflammation is modulated by a method which utilizes inositol polyaninon.

10 Claims, 7 Drawing Sheets

POLYANION ANTI-INFLAMMATORY AGENTS

This application is the national phase of PCT/US94/09492, filed Aug. 19, 1994 issued as WO 95/05830 on Mar. 2, 1995, which is a Continuation-in-Part application of U.S. application Ser. No. 08/109,642, filed Aug. 20, 1993, abandoned.

BACKGROUND OF THE INVENTION

1. Field of the Invention

This invention relates generally to the field of cell adhesion molecules and specifically to the use of inositol polyanion compositions for modulating selectin binding.

2. Description of Related Art

Cell adhesion molecules (CAMs) play a role in inflammation, infection, cancer and other disease processes. Recent advances in cloning and protein sequencing have led to the organization of CAMs into families, based on their molecular structure. Intense research has been focused on selectins, which are carbohydrate-binding proteins expressed on endothelial and leukocyte cell surfaces; integrins, which are found on the surfaces of leukocytes; and proteins of the immunoglobulin type such as intracellular adhesion molecule, ICAM-1 and 2 which occur on many different cell surfaces.

The mechanism of inflammation can be understood in terms of CAM interactions. Leukocyte adhesion to the vessel wall is a key step in the development of inflammatory and immunological processes. Adhesion molecules that support these interactions include the selecting, a group of CAMs which are named for the cell type on which they were originally identified. The selectins include E-selectin (endothelial cells), P-selectin (platelets) and L-selectin (lymphocytes).

The three selectins act in concert with other cell adhesion molecules (e.g., ICAM-1, vascular cell adhesion molecule-1 and the leukocyte integrins) to effect adhesive interactions of leukocytes, platelets and endothelial cells. E-selectin was first shown to support the adhesion of neutrophils to cytokine-activated endothelium (Bevilacqua, et al., *Proc. Natl. Acad. Sci.,* USA. 84:9238, 1987; Bevilacqua, et al., *Science* 243:1160, 1989). Subsequent studies in vitro have suggested that E-selectin also supports the binding of monocytes, a subpopulation of memory T lymphocytes, eosinophils and basophils. Similarly, P-selectin also supports leukocyte adhesion. In addition to its role in lymphocyte homing, L-selectin appears to participate in the adhesion of neutrophils, monocytes and lymphocytes to activated endothelium (reviewed in Bevilacqua, M. and Nelson, R., *J.Clin. Invest.* 91:379, 1993).

Each selectin is a transmembrane glycoprotein containing an N-terminal lectin-like domain, an epidermal growth factor repeat, and a discrete number of complement regulatory-like repeats. E- and P-selectin are expressed by activated endothelial cells while L-selectin is constitutively expressed on leukocytes and can be shed upon activation. E- and P-selectin recognize oligosaccharide structures including the tetrasaccharide, sialyl Lewis$^x$ (sLe$^x$; NeuSAcα2–3Galβ1–4(Fucα1–3)GlcNAc) that are found on leukocytes. L-selectin can bind similar structures, although recent studies suggest a substantial difference in affinities. In addition, L-selectin has been shown to bind sulfatides (sulfated glycolipids) as well as sulfate-and sialic acid-containing mucin-type glycoproteins expressed on high endothelial venules of lymph nodes. Soluble oligosaccharides related to sLe$^x$ and sLe$^a$ (a positional isomer of sLe$^x$) are able to inhibit ligand binding and adhesive functions of E- and P-selectin. These compounds have been under investigation as anti-inflammatory agents, however, their complex structures pose significant obstacles for large-scale synthesis. Previous studies have shown that phosphate- and sulfate-containing carbohydrates unrelated to sLe$^x$ can interact with P- and L-selectin. For example, PPME, the poly-phosphomonoester core of *Hansenula holstil* O-phosphonomannan, blocks L-selectin dependent adhesion. In addition, fucoidan, a sulfated polysaccharide produced by brown algae, and heparin, a sulfated glycosaminoglycan produced by mast cells, interact with both P- and L-selectin. Finally, high concentrations (typically, 5–10 mM) of phosphated monosaccharides have been shown to block P- and L-selectin dependent adhesion in vitro.

Inositol polyanions are derivatives of a six carbon ring structure (1,2,3,5-trans-4,6cyclohexanehexol; myo-inositol) esterified with phosphate or sulfate groups. Myo-inositol is one of nine known cis-trans isomers of hexahydroxycyclohexane, a 6-carbon ring structure found in abundance in plants and animals. For example, phosphatidyl inositol is a major component of cell membrane phospholipids. An expanding body of evidence indicates that many, if not all, mammalian cells contain inositol polyphosphates with 5 or more phosphate groups. Most of these inositol polyphosphates do not participate in signal transduction, however, a number of other effects in vitro and in vivo have been described. One of the best characterized of these effects is the allosteric regulation of hemoglobin affinity for oxygen by inositol pentakisphosphate (IP5) and inositol hexakisphosphate (IP6). In avian erythrocytes, IP5 binds to a specific site in the hemoglobin tetramer, increasing its affinity for oxygen. IP6 is also an effective allosteric regulator of mammalian hemoglobin in vitro. Intracellular IP5 and IP6 may also participate in other cellular functions through interactions with specific proteins.

There is little information regarding the content of IP6 in extracellular fluids, including plasma. However, several studies have suggested that extracellular IP6, as well as other inositol phosphates, may influence cell function. For example, IP6 appears to act on neutrophils to enhance their responses to activating stimuli (Crawford, et al, *Biochem. Soc. Trans.* 19:1048, 1991; Eggleton, et al., *Biochim. Biophys. Acta* 1094:309, 1991)). IP6 may also enhance the function of natural killer cells known to be involved in tumor destruction (Baten, et al, *Carcinogenesis* 10:1595, 1989). It has been suggested that 1,2,6-triphosphate (IP3) can modestly inhibit inflammation in a rodent model (Claxson, et aL, *Agents Actions* 29,1/2:68, 1990).

Many recent studies on selectin-carbohydrate interactions have focused on the tetrasaccharides sLe$^x$ and sLe$^n$. However, it has been suggested that P- and L-selectin can interact with some negatively charged polysaccharides. For example, L-selectin adhesion can be blocked by the sulfated polysaccharide fucoidan, as well as a complex core polysaccharide of yeast containing mannose-6-phosphate (Stoolman, et al., *J. Cell Biol.* 99:1535, 1984).

Inflammatory and immunological responses are essential for host defense. Under certain circumstances control mechanisms appear to fail and the responses become extreme. Resulting tissue damage contributes to human disease processes such as adult respiratory distress syndrome and rheumatoid arthritis. An early event in inflammation is focal adhesion to leukocytes to the vessel wall. E-, P- and L-selectin support the initial attachment of leukocytes to the inflamed vascular endothelium through their recognition of carbohydrate ligands such as sLe$^x$.

There is a need to identify compositions which have anti-inflammatory and biocompatible properties. The present invention provides such compositions.

SUMMARY OF THE INVENTION

The present invention provides a method of modulating selectin binding in a subject comprising administering to the subject an effective amount of an inositol polyanion which binds to the selectin. Preferably, the inositol polyanion binds to the P- and L-selectin. The inositol polyanions of the invention are preferably inositol phosphates or inositol sulfates with 5 or more phosphates or sulfates.

The function of selectins suggests their involvement in a wide variety of human diseases associated with inflammation. These range from acute appendicitis to asthma, myocardial infarction, specific immunological disease processes, infection with viruses or bacteria, malignancy and metastasis, and reperfusion injury. Antiinflammatory compounds which are inositol polyphosphates or polysulfates, which block selectin-dependent adhesion directly, would be useful in modulating the selectin-dependent adhesion associated disorders in a subject.

DETAILED DESCRIPTION OF THE INVENTION

Figure 1A:
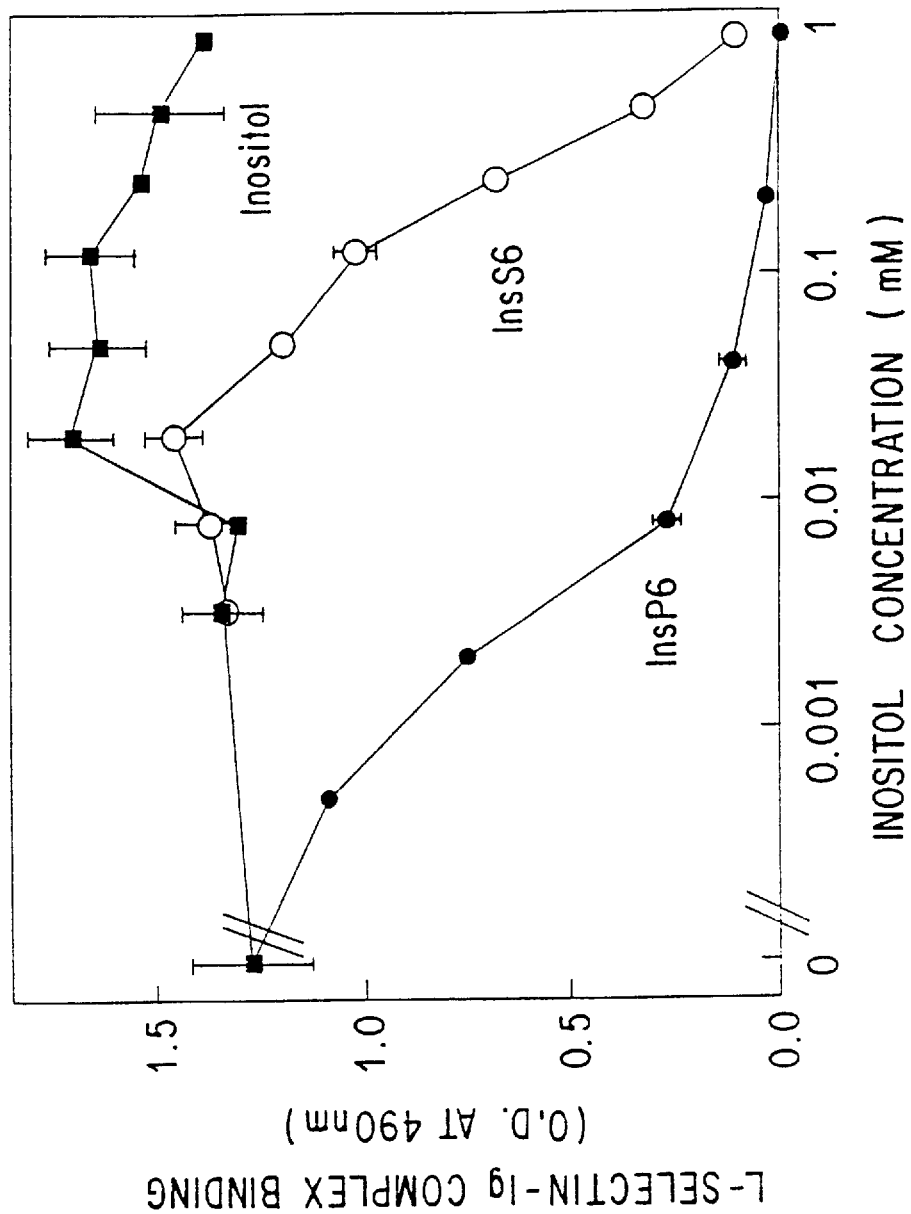
FIGS. 1a–1c show the effect of myo-inositols on the binding of L-(FIG. 1a), P (FIG. 1b) and E-selectin-lg (FIG. 1c) fusion proteins to immobilized BSA-sLe$^x$ in a competition ELISA.

The present invention provides a method of modulating selectin binding in a subject comprising administering to the subject an effective amount of an inositol polyanion which binds to the selectin. Preferably, the inositol polyanion is used in ameliorating P- and L-selectin binding associated disorders such as inflammatory processes, specific immunological disease processes, infection with viruses or bacteria, malignancy and metastasis, and reperfusion injury, for example.

The term "modulate" refers to controlling the binding of a natural ligand to the selectin by blocking the interaction using an inositol polyanion which binds the selectin. The inositol polyanion is useful for ameliorating a disorder associated with selectin binding in a subject. The term "ameliorate" denotes a lessening of the detrimental effect of the selectin binding associated disease in the subject receiving therapy. The method of the invention is useful for ameliorating the disease by administering an inositol polyanion which preferably has phosphate or sulfate groups to inhibit binding of a natural ligand to a selectin. Preferably, the selectin in the method of the invention is the P- or L-selectin.

An effective amount of the inositol polyanion is administered to the subject according to the method of the invention. The term "effective amount" refers to that amount of inositol polyanion which is administered in sufficient quantity to bind to the selectin to block the natural ligand from binding, thereby ameliorating any selectin binding associated disorder.

Since leukocyte adhesion to the vascular wall is a key, early step in inflammation, therapies directed at preventing this step are attractive for the treatment of pathologic inflammation. E- and P- selectin expression is induced in endothelial cells (and platelets in the case of P-selectin) rather than constitutive and, therefore, concentrated in areas of inflammation. L-selectin is constitutively expressed in leukocytes and shed upon cell activation. This means that adhesion inhibitors would only be required locally and, consequently, would be effective at lower doses than inhibitors aimed at broadly expressed molecules. Such therapies may be cheaper and less toxic than currently available therapies.

The term "polyanion" refers to an inositol isomer which contains greater than one anionic group. The inositol polyanion used in the method of the invention has the following structure:

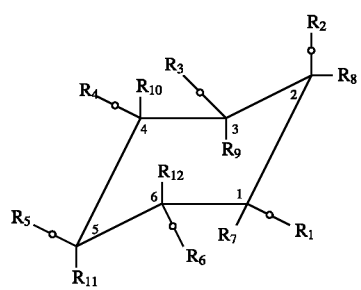

wherein $R_1, R_2, R_3, R_4, R_5, R_6, R_7, R_8, R_9, R_{10}, R_{11}$, and $R_{12}$ are each selected from the group consisting of hydrogen, phosphate anion, sulfate anion, and pyrophosphate with the proviso that at least two of $R_1, R_2, R_3, R_4, R_5$ and $R_6$ are other than hydrogen and further with the proviso that when all three of $R_1, R_2$, and $R_6$ are other than hydrogen, at least one of $R_3, R_4$, and $R_5$ is phosphate anion or sulfate anion.

Alternatively, the inositol polyanion used in the method of the invention has the following structure:

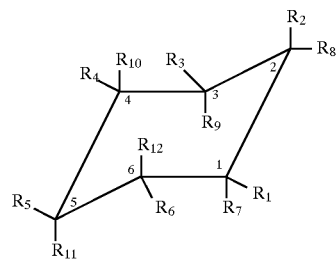

wherein $R_1, R_2, R_3, R_4, R_5, R_6, R_7, R_8, R_9, R_{10}, R_{11}$, and $R_{12}$ are each selected from the group consisting of hydrogen, phosphate anion, sulfate anion, and pyrophosphate with the proviso that at least two of $R_1, R_2, R_3, R_4, R_5$ and $R_6$ are other than hydrogen and further with the proviso that when all three of $R_1, R_2$, and $R_6$ are other than hydrogen, at least one of $R_3, R_4$, and $R_5$ is phosphate anion or sulfate anion.

Preferably the inositol polyanion used in the method of the invention is an inositol phosphate. The inositol polyanion may be an isomer of inositol phosphate or sulfate and contains from about 2 to about 6 phosphate or sulfate groups on the inositol ring. However, when positions 1, 2 and 6 contain a phosphate or sulfate, at least one of the remaining positions, 3, 4 and 5, must contain a phosphate or sulfate. Preferably the inositol phosphate of the invention contains phosphate groups at all 6 positions and is therefore a hexakisphosphate (IP6). Preferably the inositol sulfate is a hexakissulfate (IS6). The inositol polyanion may also include carboxyl (—COOH) and phosphonate (—$PO_3$) substitutions.

The inositol polyanions of the invention include polyanions which are modified, for example, by the addition or removal of functional groups, as long as the polyanion is still capable of binding to and blocking a selection. Such modifications include addition or removal of sulfate groups, addition of phosphate groups and addition of hydrophobic groups such as aliphatic or aromatic aglycones. Modifications also include the addition of residues such as sialic acid, galactose, fucose, glucose, glucuronic acid, id uranic acid, glycocyamine, N-acetyl-glycocyamine, monosaccharide, oligosaccharide, polysaccharide, Lewis$^x$, sialyl Lewis$^x$, and xylose.

Synthesis of the inositol polyanions of this invention is well known in the art. For instance, U.S. Pat. Nos. 5,274,161 and 5,128,332, which are incorporated herein in their entirety, disclose methods for synthesizing such compounds. See also European Patent Application 0 508 488 A2; PCT Application PCT/SE91/00439 and L. Stephens, et al., *J. Biol. Chem.*, 268:4009–4015,1993.

The inositol polyanions useful in the method of the invention may be a mixture of molecules containing different isomers of inositol polyphosphates or polysulfates or both, or may be a homogeneous composition. In addition, the polyanion units may be multimerized using the same or different isomers joined by a spacer moiety. Those of skill in the art can produce various combinations of the appropriate inositol polyanions without resort to undue experimentation.

The inositol polyanion may be administered to a patient according to the method of the invention to ameliorate P- and L-selectin receptor binding associated disorders, for example. One such disorder in which the inositol polyanion may be administered to a patient is for the treatment of inflammation. The inositol polyanions used in the method of the invention can be administered parenterally by injection or by gradual perfusion over time. The inositol polyanions can also be administered intravenously, intraperitoneally, intramuscularly, subcutaneously, intracavity, or transdermally. Inositol polyanions may also be administered orally or by inhalation. For example, when used therapeutically for treatment of an inflammatory disorder of the lungs, a preferred route of administration would be by a pulmonary aerosol. By blocking the P- and L-selectin receptors, leukocyte adhesion to endothelium at the site of inflammation is blocked.

Administration of the inositol polyanion in the method of the invention may also be used for ameliorating post-reperfusion injury. When treating arterial thrombosis, induction of reperfusion by clot lysing agents such as tissue plasminogen activator (t-PA) is often associated with tissue damage. Such tissue damage is thought to be mediated at least in part by leukocytes including but not limited to polymorphonuclear leukocytes (PMN). Therefore administration of the inositol polyanion would block leukocyte or PMN-endothelial interactions, and thereby diminish or prevent post-reperfusion injury.

The method of the invention can also be used to prevent adhesion of leukocyte tumor cells or non-leukocyte tumor cells to endothelial tissue. Thus, administration of a hexakissphosphate or hexakissulfate, for example, which binds to a selectin, such as P- or L- for example, would prevent metastatic spread of tumor cells.

The method of the invention is also useful for the treatment of microbial infections. Many microbes, such as bacteria, rickettsia, various parasites, and viruses, bind to vascular endothelium and leukocytes, and in some cases, possibly to P- and L-selectin. Thus, the inositol polyanions used in the method of the invention may be administered to a patient to prevent binding of a microbe which uses a selectin receptor as its binding target molecule, thereby modulating the course of the microbial infection.

The method of the invention can be used to treat vasculitis by administering to a patient the inositol polyanion described above. Tissue damage associated with focal adhesion of leukocytes to the endothelial lining of blood vessels is inhibited by blocking the P- and L-selectin. While Applicant does not wish to be bound by this theory, it is believed that the selectin binding is an important mediator of vasculitis.

The dosage ranges for the administration of the inositol polyanions in the method of the invention are those large enough to produce the desired effect in which the symptoms of the P- and L-selectin receptor associated disease are ameliorated. The dosage should not be so large as to cause adverse side effects. Generally, the dosage will vary with the age, condition, sex and extent of the disease in the patient and can be determined by one of skill in the art. The dosage can be adjusted by the individual physician in the event of any complication. When used for the treatment of inflammation, post-reperfusion injury, leukemia, lymphoma, microbial/viral infection, vasculitis, or inhibition of the metastatic spread of tumor cells, for example, the inositol polyanion may be administered at a dosage which can vary from about 1 mg/kg to about 1000 mg/kg, preferably about 1 mg/kg to about 50 mg/kg, in one or more dose administrations daily, for one or several days. For certain long term disease processes (e.g., rheumatoid arthritis) the inositol polyanion may be administered regularly or intermittently for a period of weeks to months or years.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

Controlled delivery may be achieved by selecting appropriate macromolecules, for example, polyesters, polyamino acids, polyvinyl pyrrolidone, ethylene-vinylacetate, methylcellulose, carboxymethylcellulose, protamine sulfate, or lactide/glycolide copolymers. The rate of release of the inositol polyanion may be controlled by altering the concentration of the macromolecule.

Another method for controlling the duration of action comprises incorporating the inositol polyanions into particles of a polymeric substance such as polyesters, polyamino acids, hydrogels, polylactide/glycolide copolymers, or ethylenevinylacetate copolymers. Alternatively, it is possible to entrap the inositol polyanions in microcapsules prepared, for example, by coacervation techniques or by interfacial polymerization, for example, by the use of hydroxymethylcellulose or gelatin-microcapsules or poly(methylmethacrolate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

The following examples are intended to illustrate but not limit the invention. While they are typical of those that might be used, other procedures known to those skilled in the art may alternatively be used.

EXAMPLE 1

Effect of MYO-Inositols on the Binding of Selectins

Selectin-lg fusion proteins are recombinant chimeric molecules containing extracellular regions of selectins coupled to the hinge, CH2, and CH3 regions of human IgG1 (Aruffo, A., et al., *Cell,* 67:35, 1991; Walz, G., et al., *Science,* 250:1132, 1990). Each selectin-lg contains the lectin domain, epidermal growth factor domain, and one (L-selectin-lg), two (P-selectin-lg) or six (E-selectin-lg) complement regulatory repeats of the parent molecules. DNAs encoding selectin-Ig inserted in pCDM7 allowed transient expression of recombinant proteins in COS cells as previously described (Seed, B., et al., *Proc. Natl. Acad. Sci., U.S.A.,* 84:3365, 1987; Aruffo, A., *Current Protocols In Molecular Biology,* eds. Ausubel, F. M., et al, 16:13.1, Greene Publishing Associates and Wiley-lnterscience, New York, N.Y., 1992). These DNAs were also ligated into pNUT (Palmiter, R. D., et al, *Cell,* 50:435, 1987) for amplification and stable expression in BHK cells. The fusion proteins were affinity purified from culture media using protein A (Pierce Chemical Company, Rockford, Ill.) or protein G (Pharmacia, Piscataway, N.J.) Sepharose, as previously described (Aruffo, A., et al., *Cell,* 67:35, 1991; Aruffo, A., *Current Protocols In Molecular Biology,* eds. Ausubel, F. M., et al, supra, 1992). Competition binding ELISAs using P- and E-selectin-lg were performed essentially as described (Nelson, R. M., et al., *J. Clin. Invest.,* 91:1157, 1993), except that the assay buffer was 20 mM HEPES pH 7.4, 150 mM NaCl, 2 mM $CaCl_2$, and 0.25 mM thimerosal, containing 10 mg/ml BSA, protease-free, (Miles Inc., Kankakee, Ill.). Selectin concentrations were from 10 to 30 nM. Most preparations of L-selectin-lg showed little or no binding at these concentrations. To increase L-selectin binding, an assay similar to that previously described was used (Foxall, C., et al., *J. Cell Biol.,* 117:895, 1992), in which the L-selectin-lg (10–20 nM) was allowed to form aggregates with HRP-conjugated anti-lg antibody for 30 minutes prior to addition of inositols and incubation on the BSA-sLe$^x$-coated plate. $IC_{50}$ values were calculated by fitting binding data to the equation: fraction of maximal binding=$IC_{50}$÷($IC_{50}$+[inositol]) using nonlinear least squares analysis software (Origin, Microcal Inc, Northampton, Mass.). InsP6 (dodecasodium salt), InsS6 (hexapotassium salt), myo-inositol 1 monophosphate (cyclohexylammonium salt), and myo-inositol were from Sigma Chemical Company (St. Louis, Mo.). Stock solutions were prepared daily in 0.9% NaCl and sterilized by 0.22 μm filtration. InsP6 solutions were adjusted at pH 7.4 with HCl.

Figure 1B:
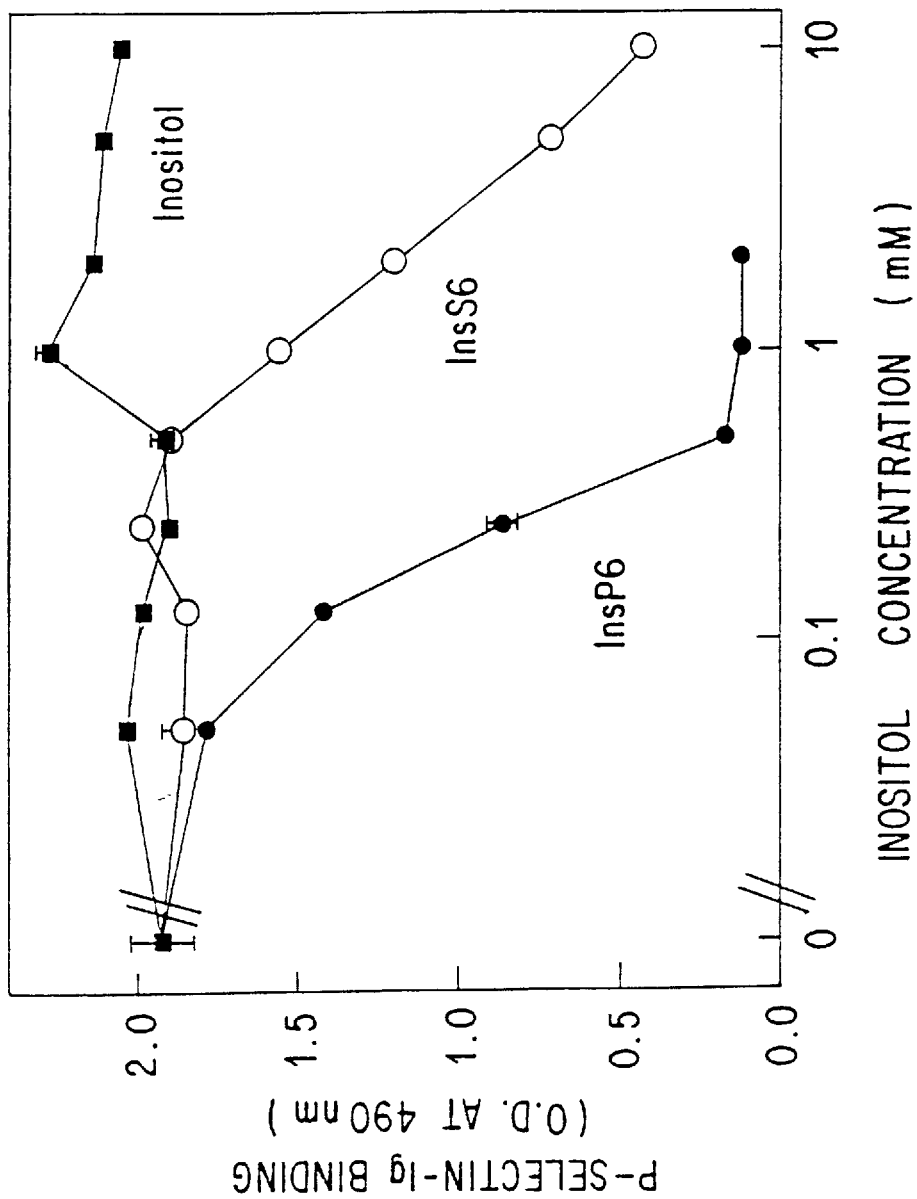
Figure 1C:
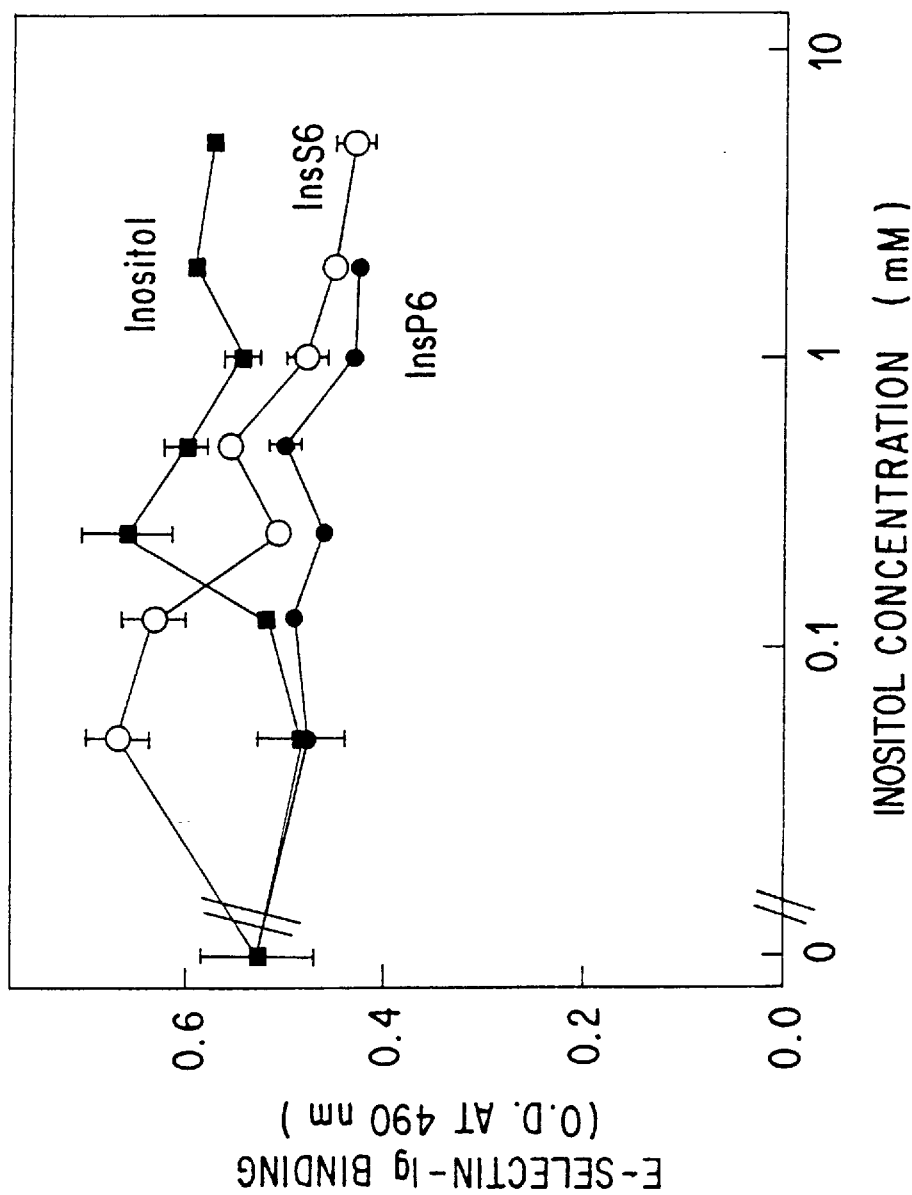

FIG. 1 shows the effect of myo-inositols on the binding of L-(FIG. 1a), P-(FIG. 1b) and E-selectin-lg (FIG. 1c) fusion proteins to immobilized BSA-sLe$^x$ in a competition ELISA. L-, P-, or E-selectin-lg fusion proteins were incubated for 2–3 hours on microtiter plates coated with the neoglycoprotein BSA-sLe$^x$, the plates washed, and bound selectin-lg was detected using a peroxidase-conjugated antibody directed against the lg portion and a chromogenic substrate. To determine blocking activity, solution-phase lnsP6 (●), InsS6 (○), or inositol (■) at the indicated concentrations were added to the solutions containing selectin-Ig fusion proteins prior to transfer to microtiter plates (competition ELISA).

As depicted in FIG. 1a and 1b, myo-inositol hexakisphosphate (InsP6) and myo-inositol hexakissulfate (InsS6), but not myo-isositol, blocked binding of L- and P-selectin immunoglobulin fusion proteins (selectin-lg) to immobilized bovine serum albumin-sLe$^x$ neoglycoprotein (BSA-sLe$^x$) in enzyme-linked immunosorbent assays (competition ELISAs). The concentration of InsP6 required to inhibit L-selectin binding by 50% ($IC_{50}$) was determined to be 3.1±0.5 μM. InsS6 was less active, showing an $IC_{50}$ value of 210±110 μM. By comparison, solution-phase sLe$^x$ tetrasaccharide failed to block L-selectin binding at concentrations up to 1 mM. InsP6 and InsS6 also blocked P-selectin binding to immobilized BSA-sLe$^x$ ($IC_{50}$=160±40 μM and 3.2±0.5 mM, respectively; FIG. 1b), whereas they failed to inhibit the binding of E-selectin-lg at concentrations up to 5 mM (FIG. 1c). As previously reported (Nelson, R. M., et al., *J. Clin. Invest.,* 9:1157, 1993; Foxall, C., et al., *J. Cell Biol,* 117:895, 1992), solution-phase sLe$^x$ was found to be an effective blocker of E-selectin ($IC_{50}$=510±60 μM).

EXAMPLE 2

Effect of an Ion Chelator on Polyanion Selectin Blocking

InsP6 binds several cations, including calcium (Kd≈5 μM). Four lines of evidence indicate that $Ca^{2+}$ sequestration by InsP6 was not responsible for selectin blocking in our studies. First, lnsP6 did not block E-selectin-lg binding to BSA-SLE$^x$. Second, EDTA, a strong $Ca^{2+}$ chelator (Kd≈10 pM), showed no blocking of any selectin up to a concentration of 1 mM in assay buffer, and displayed the same inhibition profile on all three selectins at concentration above 1 mM. Third, when the $Ca^{2+}$ concentration in the assay buffer was reduced to 0.15 mM, blocking of L- and P-selectin-lg by InsP6 was not enhanced. Finally, L- and P-selectin interactions with sulfatides are largely unaffected by the presence of calcium chelators such as EDTA (Suzuki, Y., et al., *Biochem. Biophys. Res. Commun.,* 190:426, 1993; Foxall, C., et al., *J. Cell Biol.,* 117:895, 1992; Nelson, R. M., et al., *Symposia on Quant. Biol.,* 57:271, 1992). lnsP6 and lnsS6 (but not inositol) blocked selectin-sulfatide interactions at concentrations similar to those that were effective in blocking the binding to BSA-sLe$^x$.

EXAMPLE 3

Effect of InsP6 on the Adhesion of Cancer Cells to Selectins

Cell adhesion assays on immobilized selectin-lg were performed essentially as described (Nelson, R. M., et al., *J. Clin. Invest.,* 91:1157, 1993; Nelson, R. M., et al., *Symposia on Quant. Biol.,* 57:271, 1992). Briefly, Nunclon Terasaki Microwell plates were coated overnight with 5 μl/well of a 5 μg/ml solution of protein A (Chemicon, Temecula, Calif.) in 50 mM carbonate buffer, pH 9.5. Protein-A-coated plates were washed with Dulbecco's phosphate buffered saline (PBS), incubated for 1 hour with L-, P-, or E-selectin-Ig fusion proteins in PBS (5–20 μg/ml), washed again, and blocked with PBS containing 1% human serum albumin (HSA). To measure inhibition of cell adhesion, 5 μl/well of lnsP6 in PBS was added to the selectin-Ig coated plates and incubated for 30 min at 40° C. LS 180 cells were harvested by brief trypsinization and resuspended at $1.5 \times 10^6$ cells/ml in PBS containing 1% HSA; five μl/well of suspension was added, and incubated for 30 min at 4° C. After washing to remove unbound cells, adherent cells were fixed with glutaraldehyde (2.5% in PBS) and counted. Symbols and error bars represent mean number of adherent cells/mm$^2$±s.e.m., counted in quadruplicate wells in a single experiment representative of three. No LS 180 cell adhesion was detected on plates coated with protein A alone, or on plates coated with protein A-captured CD8-Ig fusion protein. LS 180 cell adhesion was blocked by specific monoclonal antibodies directed against the appropriate selectin: LAM 1.3 (L-selectin) (Spertini, O., et al, *J. Immunol.* 147:942, 1991) G-1 (P-selectin) (Geng, J-G., et al., *J. Biol. Chem.,* 266:22313, 1991) H18/7 (E-selectin) (Bevilacqua, M. P., et al., *Proc. Natl. Acad. Sci.* USA, 84:9238, 1987).

Figure 2:
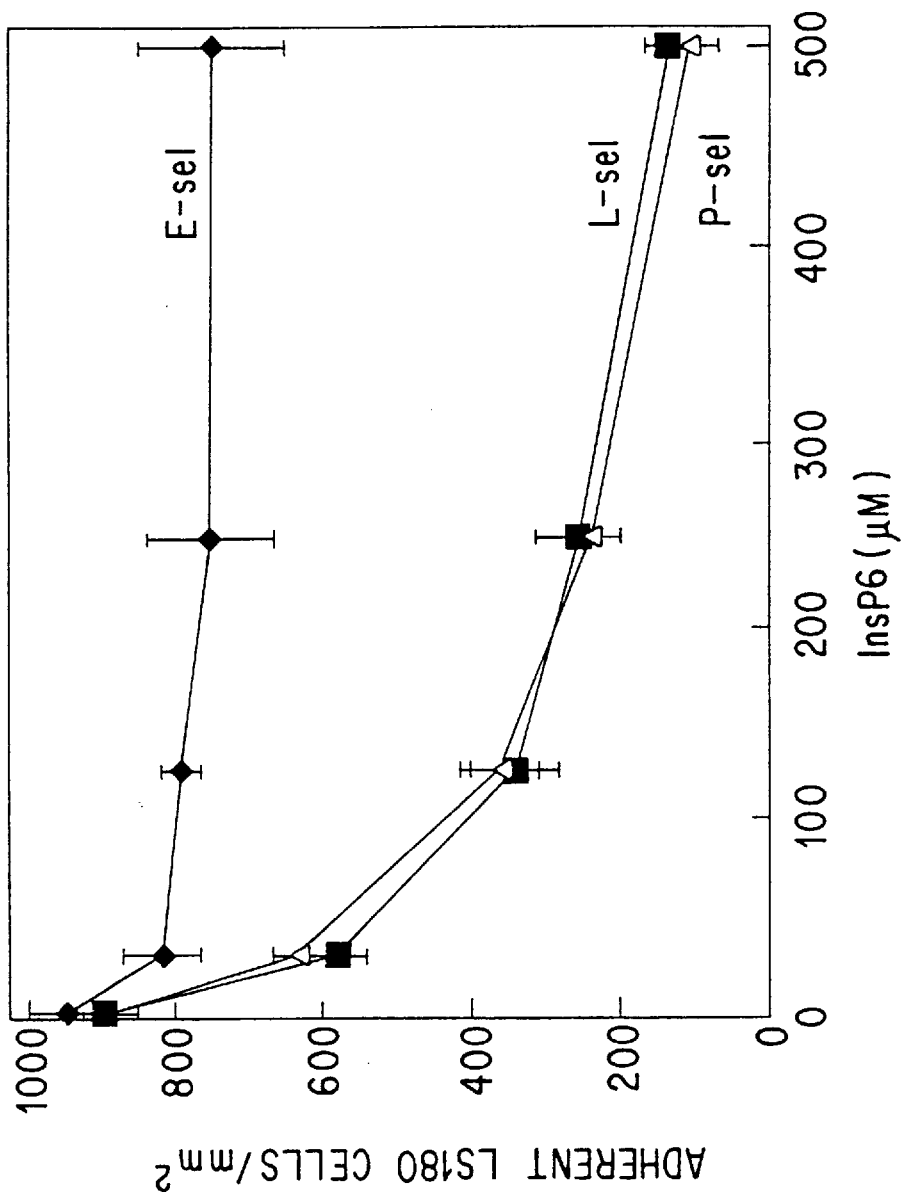
FIG. 2 shows the effect of inositol hexakisphosphate (IP6) on the adhesion of LS 180 colon cancer cells to immobilized L-(■), P- (Δ), and E-selectin-Ig (◆) fusion proteins.

FIG. 2 shows the effect of InsP6 on the adhesion of LS 180 colon cancer cells to immobilized L-(■), P-(Δ), and E-selectin-Ig (♦) fusion proteins. LS 180 cells (ATCC, Rockville, Md.) were added to cell culture wells containing protein A-captured selectin-Ig fusion proteins and incubated for 30 min at 4° C. to allow adhesion. The plates were washed to remove unbound cells and adherent cells were counted microscopically. To determine adhesion blocking activity, InsP6 at the indicated concentrations was added to selectin-Ig-coated wells 30 min prior to addition of LS 180 cells.

The effect of inositols on selectin-dependent cell adhesion was assessed using several in vitro assay systems. In the first, a colon cancer cell line, LS 180, was chosen because it binds to all three selecting. As shown in FIG. 2, InsP6 blocked the adhesion of LS 180 cells to plates coated with purified P- and L-selectin-Ig but not with E-selectin-Ig. In a single experiment, lnsS6 was also effective in blocking LS 180 adhesion to L-and P-selectin-Ig, but required higher concentrations (approx. 45% inhibition at 4 mM); myo-inositol was inactive at concentrations up to 5 mM. A second assay system used COS cells transfected with cDNAs encoding full length L-, P-, and E-selectin (L-COS, P-COS, and E-COS, respectively). lnsP6 (0.5 mM) blocked LS 180 cell adhesion to L- and P-COS (81±13% and 95±5% inhibition, 2 experiments) but not to E-COS (<5% inhibition) (see Example 4, below).

EXAMPLE 4

Figure 3A:
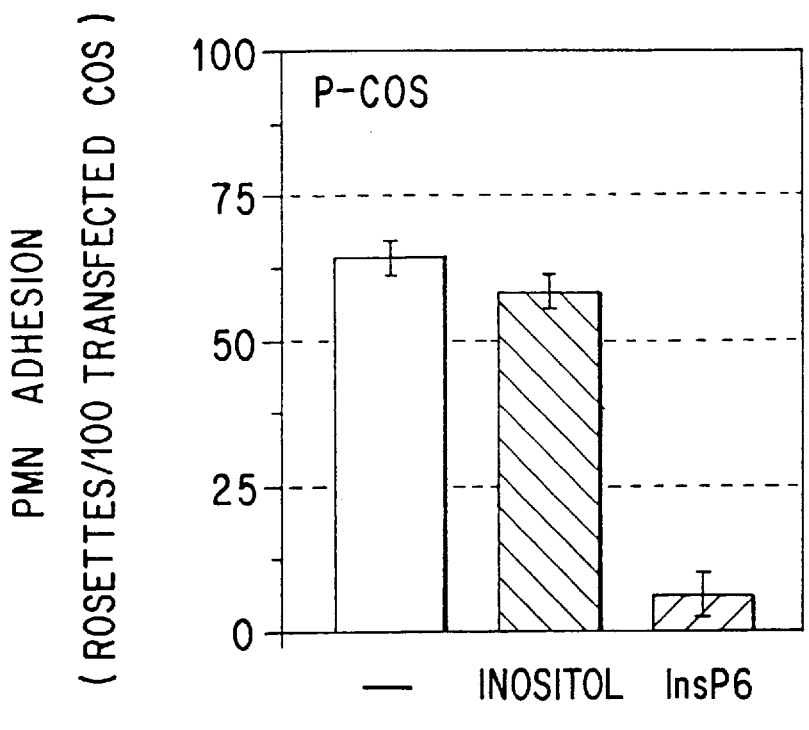
FIGS. 3a–3d show the effect of IP6 on the adhesion of isolated human polymorphonuclear leukocytes (PMN) to P-COS cells transfected with P- and E-selectin (FIG. 3a); E-COS cells transfected with P- and E-selectin (FIG. 3b); and activated endothelial monolayers under static conditions (FIG. 3c) and non-static conditions (FIG. 3d).

InsP6 Selectin Blocking in Human Polymorphonuclear Leukocytes and endothelial Cells COS-1 cells were transfected as described (Seed, B., et al., *Proc. Natl. Acad. Sci.,* U.S.A., 84:3365, 1987; Aruffo, A., *Current Protocols In Molecular Biology,* eds. supra, 1992) with pCDM7/pCDM8 expression vectors containing the full-length E-, P- and L-selectin cDNA. Transfected COS-1 cells were seeded on gelatin coated coverslips. After 72 hours to allow for cell surface expression of selecting, PMN (isolated as described (Nelson, R. M., et al., *J. Clin. Invest.,* 91:1157, 1993) or HL60 cells (106/well) were added and incubated for 30 min at 4° C. After washing to remove unbound cells, COS cells with three or more bound PMN (rosettes) were counted microscopically. Certain wells were incubated with PBS alone, or PBS containing inositol or InsP6 (0.5 mM) for 30 min prior to cell addition. Data are the mean ±s.d. of three separate experiments. Similar results were obtained with HL60. InsS6 also inhibited PMN adhesion to P-selectin transfected COS, but required higher concentrations (63% blocking at 5 mM); inositol had no effect at concentrations up to 10 mM (FIG. 3a).

Figure 3B:
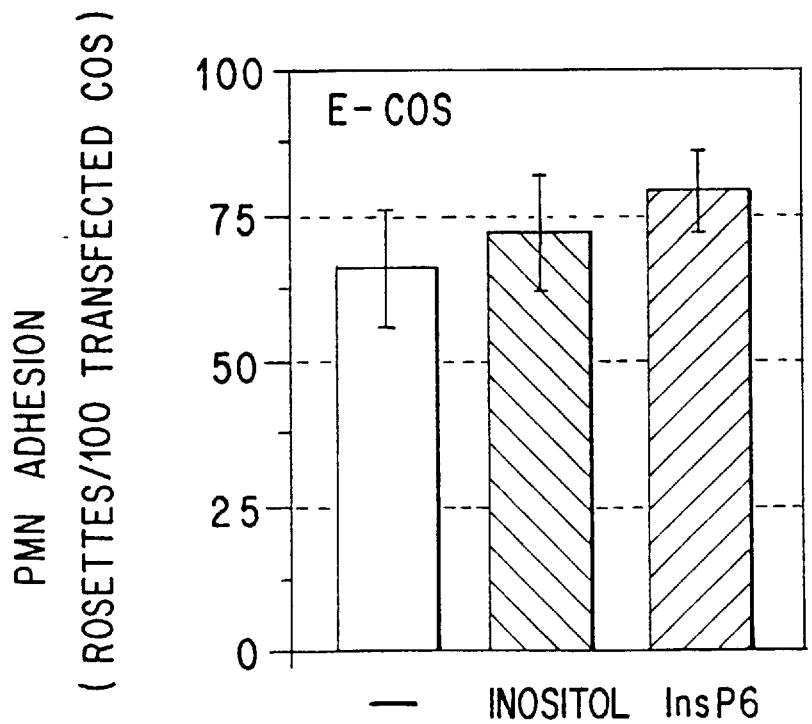
Figure 3C:
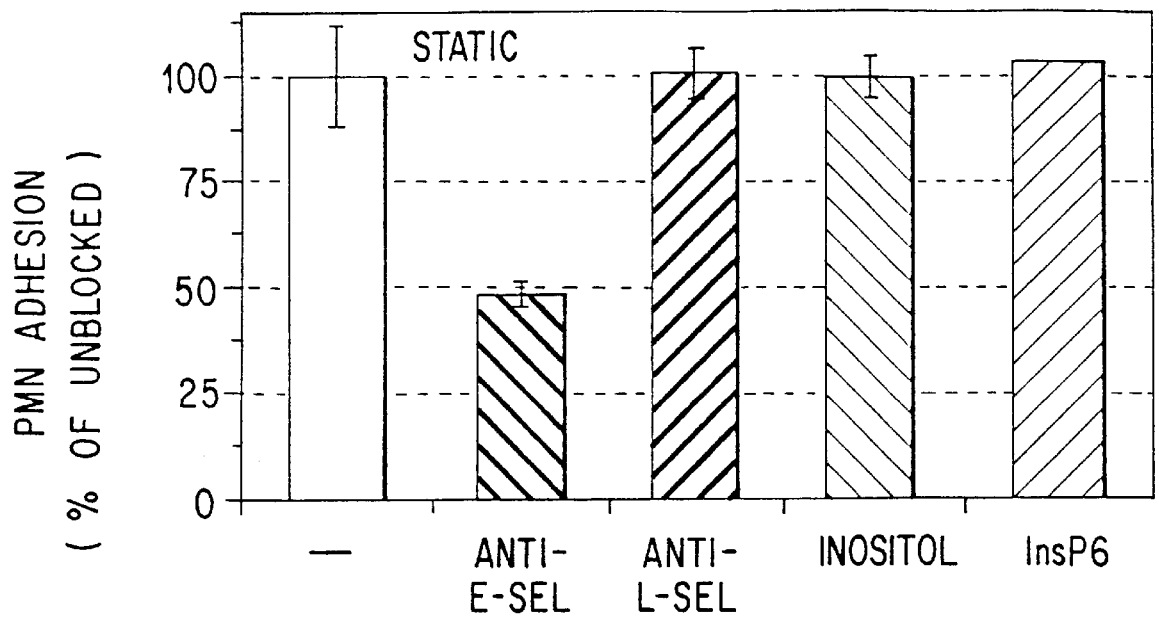
Figure 3D:
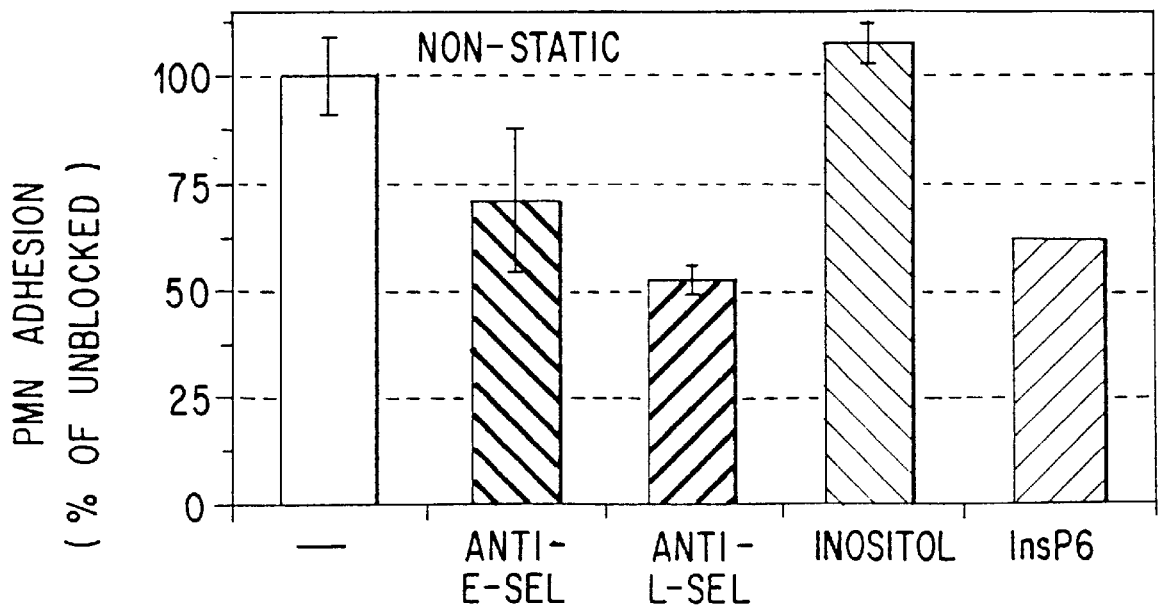

Human umbilical vein endothelial cells (HUVEC, Clonetics Corp., San Diego, Calif.) were grown to confluence with 2.2 cm diameter circles made on glass slides with a grease pencil as previously described (Spertini, O., et al., *J. Immunol.,* 147:2565, 1991), and activated for 6–8 hours at 370° C. with 200 U/ml of human recombinant TNFα (Biogen Res. Corp., Cambridge, Mass.). Human PMN ($2 \times 10^6$) were allowed to adhere to these endothelial monolayers for 30 min at 4° C. under static (stationary platform; upper panel) and non-static (rotating platform, 64 r.p.m.; lower panel) conditions. To determine adhesion blocking activity, PMN were incubated in 5% FBS in RPMI 1640 alone or containing inositol (0.5 mM), InsP6 (0.5 mM), or anti-L-selectin monoclonal antibody LAM 1.3 (10 μg/ml), for 30 min or ice prior to their addition to activated endothelial monolayers. In some experimental wells, endothelial monolayers were incubated with anti E-selectin monoclonal antibody, H18/7, for 30 min prior to addition of PMN. After washing to remove unbound PMN, cultures were fixed in PBS containing 2.5% glutaraldehyde and adherent PMN were counted microscopically. The data represent the mean ±s.e.m. of three separate experiments. Unblocked PMN adhesion to activated endothelial monolayers under static and non-static conditions ranged from 1800 to 2400 cells/mm$^2$. Unblocked adhesion to unactivated endothelium was less than 50 cells/mm$^2$ (FIG. 3b).

Isolated human polymorphonuclear leukocytes (PMN) adhered to P- and E-COS, but showed little binding to L-COS. As depicted in FIG. 3a, InsP6 (0.5 mM) blocked PMN adhesion to P-COS but not to E-COS; similar results were obtained with the promyelocytic cell line HL60.

Another assay system employed cytokine-activated endothelial monolayers under both static and non-static conditions (Spertini, O., et al., supra, 1991). Under static conditions, in which PMN adhesion to TNF-activated endothelial cells is blocked by anti-E-selectin antibodies but not by anti-L-selectin antibodies, InsP6 (0.5 mM) had little or no effect (FIG. 3b). In contrast, InsP6 blocked the adhesion of PMN to TNF-activated endothelial cells under non-static conditions (rotation-induced shear stress), in which L-selectin is known to be involved (Spertini, O., et al., supra, 1991). Taken together, these studies indicate that inositol polyanions can block cell adhesion mediated by purified L- and P-selectin-Ig fusion proteins as well as adhesion mediated by cell surface-expressed L- and P-selectin.

EXAMPLE 5

Effect of InsP6 on Inflammation In Vivo

Figure 4A:
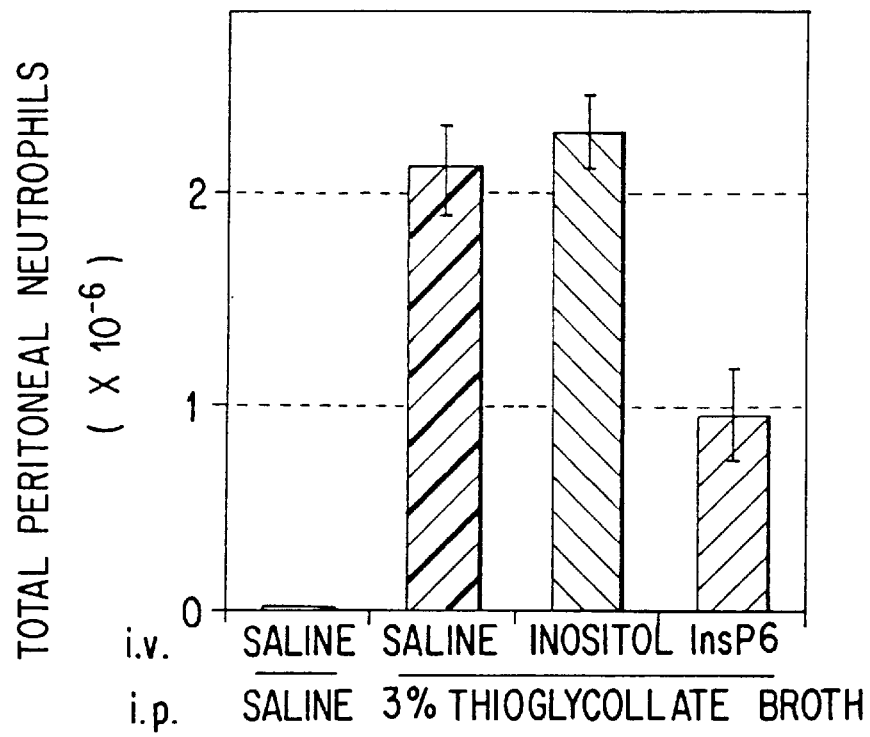
FIGS. 4a–4b show the results of in vivo administration of IP6 on acute inflammation, as determined by total peritoneal neutrophils using 3% thioglycollate broth (FIG. 4a) or zymosan (FIG. 4b) as pyrogen.
Figure 4B:
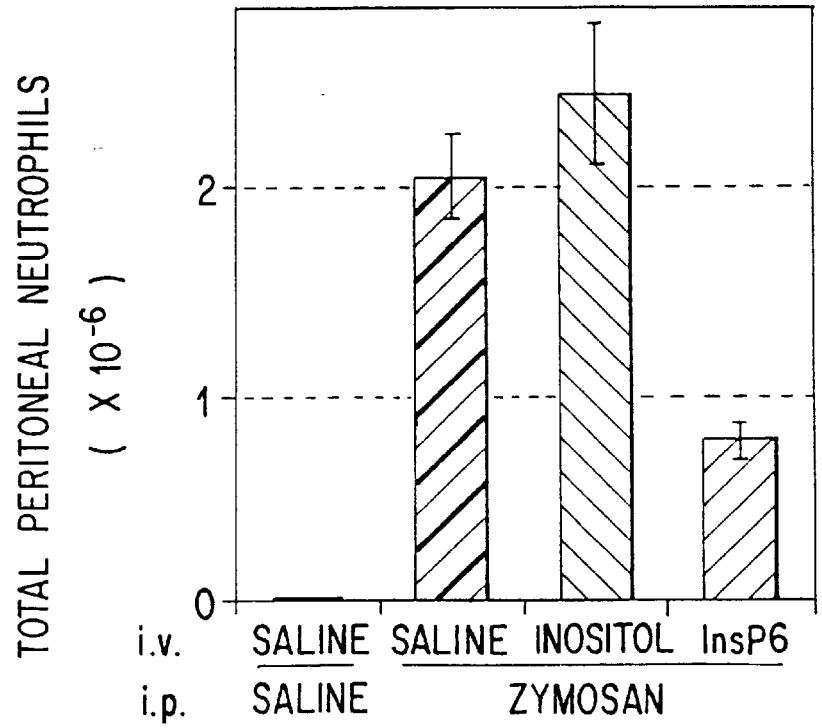

Mice (Balb/c males, 4–5 weeks old, 20–24 grams) were injected i.p. with 1 ml of 3% thioglycollate broth (lot #622462, Clinical Standard Laboratories, Inc., Rancho Dominguez, Calif.) left panel, or 0.5 mg of zymosan (Sigma) in 1 ml of sterile, pyrogen-free saline (Abbott Laboratories, North Chicago, Ill.), (FIG. 4, right panel). Control animals were injected i.p. with 1 ml of sterile pyrogen-free saline. After 40 and 80 min the animals received i.v. injections of 0.2 ml of sterile saline with or without InsP6 (total of 80 μmol/kg) or inositol (400 μmol/ kg). Mice were sacrificed at 120 min and PMN within the peritoneal cavity were collected by lavage with 10 ml of ice-cold PBS containing 10 U/ml of heparin. After red blood cell lysis, the cells were counted in a hemocytometer (2 separate counts per sample, in triplicate). The percentage of PMN was assessed by counting cytospin preparations (two counts per slide, 300 cells per count) stained with Dif-Quick stain (Baxter, McGaw Park, Ill). Data are expressed as the mean ±s.d. of three separate experiments, with 5–6 animals per group in each experiment except for the group injected with saline i.p. that was constituted by 2 animal per experiment.

It has been reported that i.v. infusion of high-dose InsP6 ($^{18}$ 600 μmol/kg) results in acute toxic effects in mice and rats when injected at a rate of 60 μmol/kg/min or higher (Gersonde, K., et al., *Toxicology.*, 22:279, 1981). In our studies, some transient (duration 1–3 min) toxic effects (unsteady gate, spasms) were noted immediately upon rapid i.v. injection (5–10 sec) of concentrated solutions of InsP6 (>50 μmol/kg). These effects were avoided by decreasing the rate of infusion and by using lower doses (40 μmol/kg). This protocol could be repeated multiple times in the same animal without apparent harmful effect. In addition, no toxic effects were observed after subcutaneous injections of InsP6 doses up to 200 μmol/kg.

In the first model, mice were given intraperitoneal (i.p.) injections of 3% thioglycollate broth (FIG. 4, left panel) which results in an accumulation of PMN, the early phase of which is thought to depend in large part on L-(Lewinsohn, D. M., et al., *J. Immunol.*, 138:4313, 1987; Watson, S. R., et al., *Nature*, 349:164, 1991), and P-selectin (Mulligan, M. S., et al., *J. Clin. Invest.*, 90:1600, 1992). Mice treated with InsP6 (i.v. injections at 40 and 80 min for a total of 80 μmol/kg) showed a 58±3% reduction (3 experiments) in PMN recovered from the peritoneal cavity at 120 min. Similar results were obtained when InsP6 (40–100 μmol/kg) was given by a single subcutaneous injection 3 min after administration of thioglycollate (46–59% inhibition). lnsP6 was found to be equally effective in a closely related murine model, zymosan-induced peritoneal inflammation (FIG. 4, right panel). InsS6 also blocked PMN accumulation in these murine models, but required significantly higher doses (400 μmol/kg, 33±13% inhibition in the thioglycollate model and 31±11% in the zymosan model, 1 experiment each). In a rat model of lung inflammation involving intratracheal instillation of endotoxin (Ulich, T. R., et al., *Am. J. Pathol*, 138:1485, 1991), InsP6 (i.v. injections at 2 and 4 hours, 40 μmol/kg total) reduced the number of PMN recovered in broncho-alveolar lavage fluid at 6 hours (59±8% inhibition, 2 experiments). The number of peripheral blood PMN was not modified by InsP6 treatment.

Inositol hexakisphosphate and inositol hexakissulfate are effective blockers of L- and P-selectin in vitro. Moreover, these molecules can reduce PMN accumulation at sites of inflammation in vivo. The selectin-blocking activity of InsP6 mediates its anti-inflammatory effects; however, the possible contribution of other mechanisms is not excluded. In selected assays, lnsP5 ($Ins_{1,3,4,5,6}P5$, Calbiochem, La Jolla, Calif.) demonstrated blocking activity in vitro against L- and P-selectin ($IC_{50}$=38±17 μM and 940±130 μM, respectively), whereas a single isomer of InsP1 had no activity. In preliminary competition ELISAs using L-selectin-lg, the L-isomer of $Ins_{1,4,5}$ P3 showed no inhibition at concentrations up to 700 μM, whereas a D, L-isomer mixture of $Ins_{1,4,6}$ P3 blocked with an $IC_{50}$=230±90 μM (single experiment). In addition, InsP5 (80 μmol/kg in two i.v. injections) reduced periotoneal influx of PMN in thioglycollate stimulated mice (48±6 % inhibition, 2 experiments).

The foregoing is meant to illustrate, but not to limit, the scope of the invention. Indeed, those of ordinary skill in the art can readily envision and produce further embodiments, based on the teachings herein, without undue experimentation.

We claim:

1. A method of blocking selectin binding in a subject with a condition associated with selectin binding comprising administering to the subject a selectin binding inhibitor amount of inositol polyanion which binds to the selectin, said polyanion having at least four anionic groups, wherein the selectin is selected from the group consisting of P-selectin and L-selectin.

2. The method of claim 1 selectin wherein the condition associated with selectin binding is inflammation.

3. The method of claim 2, wherein the inflammation is associated with a disease selected from the group consisting of arthritis, asthma, septic shock, adult respiratory distress syndrome, vasculitis, autoimmune disease and lupus erythematosus.

4. The method of claim 1, wherein the condition associated with selectin binding infection with a microorganism.

5. The method of claim 4, wherein the microorganism is a virus.

6. The method of claim 4, wherein the microorganism is a bacteria.

7. The method of claim 1, wherein the condition associated with selectin binding malignancy.

8. The method of claim 1, wherein the condition associated with selectin binding reperfusion injury.

9. The method of claim 1, wherein the inositol polyanion is a hexakis-phosphate.

10. The method of claim 1, wherein the inositol polyanion is a hexakis-sulfate.

* * * * *